(12) United States Patent
Toler et al.

(10) Patent No.: US 9,592,133 B2
(45) Date of Patent: Mar. 14, 2017

(54) SPACER BLOCK

(71) Applicant: Zimmer, Inc., Warsaw, IN (US)

(72) Inventors: Jason S. Toler, Pierceton, IN (US);
Shanon N. Roberts, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 369 days.

(21) Appl. No.: 14/034,076

(22) Filed: Sep. 23, 2013

(65) Prior Publication Data

US 2015/0088140 A1    Mar. 26, 2015

(51) Int. Cl.

| A61B 17/17 | (2006.01) |
|---|---|
| A61F 2/46 | (2006.01) |
| A61B 17/02 | (2006.01) |
| A61F 2/38 | (2006.01) |
| A61F 2/30 | (2006.01) |

(52) U.S. Cl.
CPC .......... *A61F 2/4657* (2013.01); *A61B 17/025* (2013.01); *A61B 2017/0268* (2013.01); *A61B 2090/061* (2016.02); *A61B 2090/064* (2016.02); *A61B 2090/067* (2016.02); *A61F 2/38* (2013.01); *A61F 2002/30617* (2013.01); *A61F 2002/4658* (2013.01); *A61F 2002/4668* (2013.01)

(58) Field of Classification Search
CPC ............................ A61B 17/17; A61B 17/1764
USPC .... 606/87–89, 102; 623/20.15, 20.28, 20.32, 623/20.35
See application file for complete search history.

(56) References Cited

U.S. PATENT DOCUMENTS

| 4,501,266 A | 2/1985 | McDaniel |
|---|---|---|
| 5,197,488 A | 3/1993 | Kovacevic |
| 5,344,461 A | 9/1994 | Phlipot |
| 5,360,016 A | 11/1994 | Kovacevic |
| 5,387,239 A | 2/1995 | Bianco et al. |
| 5,395,401 A | 3/1995 | Bahler |
| 5,425,775 A | 6/1995 | Kovacevic et al. |
| 5,458,637 A | 10/1995 | Hayes |
| 5,470,354 A | 11/1995 | Hershberger et al. |
| 5,489,311 A | 2/1996 | Cipolletti |
| 5,571,194 A | 11/1996 | Gabriel |

(Continued)

FOREIGN PATENT DOCUMENTS

| AU | 2011343440 B2 | 4/2014 |
|---|---|---|
| CN | 1174498 A | 2/1998 |

(Continued)

OTHER PUBLICATIONS

"U.S. Appl. No. 13/087,610, Non Final Office Action mailed Feb. 26, 2013", 7 pgs.

(Continued)

*Primary Examiner* — Christopher Beccia
(74) *Attorney, Agent, or Firm* — Schwegman Lundberg & Woessner, P.A.

(57) ABSTRACT

A knee arthroplasty system for use in a patient's knee joint comprises a spacer block instrument including a base portion, a tibial component extending from the base portion and configured for placement against a tibia, and a femoral component configured for placement against a femur. The femoral component is rotatably coupled to the tibial component. The system further includes one or more spacer block shims structured for removable attachment to the tibial component.

20 Claims, 13 Drawing Sheets

(56) References Cited

U.S. PATENT DOCUMENTS

| | | |
|---|---|---|
| 5,609,645 A | 3/1997 | Vinciuerra |
| 5,656,785 A | 8/1997 | Trainor et al. |
| 5,658,341 A | 8/1997 | Delfosse |
| 5,702,464 A | 12/1997 | Lackey et al. |
| 5,733,292 A | 3/1998 | Gustilo et al. |
| 5,776,200 A | 7/1998 | Johnson et al. |
| 5,782,925 A | 7/1998 | Collazo et al. |
| 5,824,103 A | 10/1998 | Williams |
| 5,871,541 A | 2/1999 | Gerber |
| 5,976,147 A | 11/1999 | LaSalle et al. |
| 6,607,559 B2 | 8/2003 | Ralph et al. |
| 6,632,225 B2 | 10/2003 | Sanford et al. |
| 6,702,821 B2 | 3/2004 | Bonutti |
| 6,743,258 B1 | 6/2004 | Keller |
| 6,770,078 B2 | 8/2004 | Bonutti |
| 6,942,670 B2 | 9/2005 | Heldreth et al. |
| 6,974,481 B1 | 12/2005 | Carson |
| 7,309,363 B2 | 12/2007 | Dietz |
| 7,364,581 B2 * | 4/2008 | Michalowicz ....... A61B 17/157 |
| | | 606/87 |
| 7,412,897 B2 | 8/2008 | Crottet et al. |
| 7,442,196 B2 | 10/2008 | Fisher et al. |
| 7,488,330 B2 | 2/2009 | Stad |
| 7,547,327 B2 | 6/2009 | Collazo |
| 7,575,602 B2 | 8/2009 | Amirouche et al. |
| 7,578,821 B2 | 8/2009 | Fisher et al. |
| 7,587,945 B2 | 9/2009 | Crottet et al. |
| 7,591,854 B2 | 9/2009 | Wasielewski |
| 7,632,283 B2 | 12/2009 | Heldreth |
| 7,632,314 B2 | 12/2009 | Dietz |
| 7,695,520 B2 | 4/2010 | Metzger et al. |
| 7,837,691 B2 | 11/2010 | Cordes et al. |
| 7,850,698 B2 | 12/2010 | Straszheim-Morley et al. |
| 8,065,927 B2 | 11/2011 | Crottet et al. |
| 8,141,437 B2 | 3/2012 | Amirouche et al. |
| 8,197,549 B2 | 6/2012 | Amirouche et al. |
| 8,211,041 B2 | 7/2012 | Fisher et al. |
| 8,245,583 B2 | 8/2012 | Stein |
| 8,491,589 B2 | 7/2013 | Fisher et al. |
| 8,506,571 B2 | 8/2013 | Chana et al. |
| 8,603,101 B2 | 12/2013 | Claypool et al. |
| 9,011,459 B2 | 4/2015 | Claypool et al. |
| 9,149,206 B2 | 10/2015 | Claypool et al. |
| 2002/0058997 A1 | 5/2002 | O'connor et al. |
| 2002/0072802 A1 | 6/2002 | O'Neil et al. |
| 2004/0059340 A1 * | 3/2004 | Serra .................. A61F 2/4657 |
| | | 606/102 |
| 2004/0064191 A1 | 4/2004 | Wasielewski |
| 2004/0122441 A1 * | 6/2004 | Muratsu ............ A61B 17/0206 |
| | | 606/102 |
| 2004/0167537 A1 | 8/2004 | Errico et al. |
| 2004/0225368 A1 | 11/2004 | Plumet et al. |
| 2005/0055102 A1 | 3/2005 | Tornier et al. |
| 2005/0267485 A1 | 12/2005 | Cordes et al. |
| 2006/0020343 A1 | 1/2006 | Ek |
| 2006/0052782 A1 | 3/2006 | Morgan et al. |
| 2006/0069436 A1 | 3/2006 | Sutton et al. |
| 2006/0089653 A1 * | 4/2006 | Auger ................. A61B 17/155 |
| | | 606/88 |
| 2006/0111726 A1 | 5/2006 | Felt et al. |
| 2006/0184176 A1 | 8/2006 | Straszheim-Morley et al. |
| 2006/0190087 A1 | 8/2006 | O'Connor |
| 2007/0123992 A1 | 5/2007 | Sanford |
| 2007/0234819 A1 | 10/2007 | Amirouche et al. |
| 2007/0239165 A1 | 10/2007 | Amirouche |
| 2008/0051908 A1 | 2/2008 | Angibaud |
| 2008/0091273 A1 | 4/2008 | Hazebrouck |
| 2008/0103603 A1 | 5/2008 | Hintermann |
| 2009/0125114 A1 | 5/2009 | May et al. |
| 2009/0204222 A1 | 8/2009 | Burstein et al. |
| 2009/0259314 A1 | 10/2009 | Linder-ganz et al. |
| 2009/0264894 A1 | 10/2009 | Wasielewski |
| 2009/0287310 A1 | 11/2009 | Fisher et al. |
| 2009/0306787 A1 | 12/2009 | Crabtree et al. |
| 2010/0010494 A1 | 1/2010 | Quirno |
| 2010/0063595 A1 | 3/2010 | Dietz |
| 2010/0076563 A1 | 3/2010 | Otto et al. |
| 2010/0082111 A1 | 4/2010 | Thomas |
| 2010/0100011 A1 | 4/2010 | Roche |
| 2010/0198275 A1 | 8/2010 | Chana et al. |
| 2010/0249789 A1 | 9/2010 | Rock et al. |
| 2011/0100011 A1 | 5/2011 | Staffend |
| 2012/0004580 A1 | 1/2012 | Wagner et al. |
| 2012/0095563 A1 | 4/2012 | Sanford et al. |
| 2012/0158152 A1 * | 6/2012 | Claypool ................ A61F 2/389 |
| | | 623/20.33 |
| 2012/0179069 A1 | 7/2012 | Amirouche |
| 2012/0232429 A1 | 9/2012 | Fischer et al. |
| 2012/0290088 A1 | 11/2012 | Amirouche et al. |
| 2013/0013076 A1 | 1/2013 | Fisher et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0253378 A1 | 9/2013 | Claypool et al. |
| 2013/0261504 A1 | 10/2013 | Claypool et al. |
| 2013/0261757 A1 | 10/2013 | Claypool et al. |
| 2013/0261758 A1 | 10/2013 | Claypool et al. |
| 2014/0052269 A1 | 2/2014 | Claypool et al. |
| 2014/0296859 A1 | 10/2014 | Claypool et al. |
| 2015/0190243 A1 | 7/2015 | Claypool et al. |

FOREIGN PATENT DOCUMENTS

| | | |
|---|---|---|
| CN | 101522136 A | 9/2009 |
| CN | 101711701 A | 5/2010 |
| CN | 101835441 A | 9/2010 |
| CN | 103370025 A | 10/2013 |
| CN | 103379880 A | 10/2013 |
| CN | 104379094 A | 2/2015 |
| CN | 104736105 A | 6/2015 |
| EP | 0903125 A1 | 3/1999 |
| EP | 1132063 A2 | 9/2009 |
| EP | 2237177 A1 | 10/2010 |
| EP | 2830543 A1 | 2/2015 |
| EP | 2830544 A1 | 2/2015 |
| JP | 61247449 A | 11/1986 |
| JP | 09289998 A | 11/1997 |
| JP | 2009245619 A | 10/2009 |
| JP | 2015512307 A | 4/2013 |
| JP | 2014505517 A | 3/2014 |
| JP | 2014508554 A | 4/2014 |
| JP | 2014239900 A | 12/2014 |
| JP | 2015513966 A | 5/2015 |
| WO | WO-2010022272 A1 | 2/2010 |
| WO | WO-2010023062 A2 | 3/2010 |
| WO | WO-2012004580 A1 | 1/2012 |
| WO | WO-2012020460 A1 | 2/2012 |
| WO | WO-2013013094 A1 | 1/2013 |
| WO | WO-2013148954 A1 | 10/2013 |
| WO | WO-2013148960 A1 | 10/2013 |

OTHER PUBLICATIONS

"U.S. Appl. No. 13/087,610, Notice of Allowance mailed Jun. 28, 2013", 6 pgs.

"U.S. Appl. No. 13/087,610, Notice of Allowance mailed Oct. 8, 2013", 7 pgs.

"U.S. Appl. No. 13/087,610, Response filed May 24, 2013 to Non Final Office Action mailed Feb. 26, 2013", 15 pgs.

"U.S. Appl. No. 13/819,116, Preliminary Amendment filed Feb. 26, 2013", 8 pgs.

"U.S. Appl. No. 13/819,116, Restriction Requirement mailed Feb. 12, 2015", 7 pgs.

"U.S. Appl. No. 13/836,586, Express Abandonment filed May 30, 2014", 1 pg.

"U.S. Appl. No. 13/836,665, Examiner Interview Summary mailed Jul. 17, 2014", 4 pgs.

"U.S. Appl. No. 13/836,665, Final Office Action mailed Jul. 25, 2014", 25 pgs.

"U.S. Appl. No. 13/836,665, Non Final Office Action mailed Jan. 30, 2014", 21 pgs.

(56) References Cited

OTHER PUBLICATIONS

"U.S. Appl. No. 13/836,665, Response filed Jan. 23, 2015 to Final Office Action mailed Jul. 25, 2014", 25 pgs.
"U.S. Appl. No. 13/836,665, Response filed May 30, 2014 to Non-Final Office Action mailed Jan. 30, 2014", 21 pgs.
"U.S. Appl. No. 13/837,774, Examiner Interview Summary mailed Jul. 22, 2014", 4 pgs.
"U.S. Appl. No. 13/837,774, Final Office Action mailed Jul. 28, 2014", 17 pgs.
"U.S. Appl. No. 13/837,774, Non Final Office Action mailed Feb. 10, 2014", 33 pgs.
"U.S. Appl. No. 13/837,774, Response filed Jan. 28, 2015 to Final Office Action mailed Jul. 28, 2014", 16 pgs.
"U.S. Appl. No. 13/837,774, Response filed Jun. 10, 2014 to Non-Final Office Action mailed Feb. 20, 2014", 29 pgs.
"U.S. Appl. No. 14/063,032, Non Final Office Action mailed Jun. 20, 2014", 6 pgs.
"U.S. Appl. No. 14/063,032, Notice of Allowance mailed Dec. 19, 2014", 6 pgs.
"U.S. Appl. No. 14/063,032, Preliminary Amendment filed Oct. 25, 2013", 3 pgs.
"U.S. Appl. No. 14/063,032, Response filed Oct. 20, 2014 to Non-Final Office Action mailed Jun. 20, 2014", 9 pgs.
"U.S. Appl. No. 14/304,009, Preliminary Amendment filed Jul. 31, 2014", 7 pgs.
"U.S. Appl. No. 14/660,217, Preliminary Amendment filed Mar. 18, 2015", 9 pgs.
"Australian Application Serial No. 2011343440, First Examiner Report mailed Feb. 17, 2014", 3 pgs.
"Australian Application Serial No. 2011343440, Response filed Mar. 21, 2014 to Office Action mailed Feb. 17, 2014", 1 pg.
"Canadian Application Serial No. 2,821,927, Voluntary Amendment mailed Jun. 14, 2013", 7 pgs.
"Canadian Application Serial No. 2,824,527, Office Action mailed Mar. 17, 2014", 2 pgs.
"Canadian Application Serial No. 2,824,527, Response filed Sep. 17, 2014 to Office Action mailed Mar. 17, 2014", 14 pgs.
"Chinese Application Serial No. 201180067430.X, Office Action mailed Aug. 28, 2014", (W/ English Translation), 8 pgs.
"Chinese Application Serial No. 201180067430.X, Response filed Jan. 4, 2015 to Office Action mailed Sep. 26, 2014", (W/ English Translation), 14 pgs.
"Chinese Application Serial No. 201180067757.7, Voluntary Amendment mailed Feb. 14, 2014", (W/ English Translation of Claims), 8 pgs.
"European Application Serial No. 11808493.8, Examination Notification Art. 94(3) mailed Feb. 20, 2015", 6 pgs.
"International Application Serial No. PCT/US2011/064435, International Preliminary Report on Patentability mailed Jun. 27, 2013", 9 pgs.
"International Application Serial No. PCT/US2011/064435, Search Report mailed Jun. 21, 2012", 5 pgs.
"International Application Serial No. PCT/US2011/064435, Written Opinion mailed Jun. 21, 2012", 7 pgs.
"International Application Serial No. PCT/US2011/065683, International Preliminary Report on Patentability mailed Jun. 27, 2013", 11 pgs.
"International Application Serial No. PCT/US2011/065683, International Search Report mailed Apr. 24, 2012", 12 pgs.
"International Application Serial No. PCT/US2011/065683, Written Opinion mailed Apr. 24, 2012", 10 pgs.
"International Application Serial No. PCT/US2013/034286, International Preliminary Report on Patentability mailed Oct. 9, 2014", 8 pgs.
"International Application Serial No. PCT/US2013/034286, International Search Report mailed Jun. 25, 2013", 6 pgs.
"International Application Serial No. PCT/US2013/034286, Written Opinion mailed Jun. 25, 2013", 6 pgs.
"International Application Serial No. PCT/US2013/034293, International Preliminary Report on Patentability mailed Oct. 9, 2014", 9 pgs.
"International Application Serial No. PCT/US2013/034293, International Search Report mailed Jun. 25, 2013", 6 pgs.
"International Application Serial No. PCT/US2013/034293, Written Opinion mailed Jun. 25, 2013", 7 pgs.
"Japanese Application Serial No. 2013-544858, Request for Examination filed Feb. 4, 2014", (With English Translation), 14 pgs.
"Zimmer NexGen Trabecular Metal Tibial Tray", Surgical Technique, Zimmer, Inc., (2007, 2009), 16 pgs.
"Zimmer Patient Specific Instruments", Surgical Techniques for NexGen Complete Knee Solution Zimmer, Inc., (2010), 16 pgs.
"U.S. Appl. No. 13/836,665, Notice of Allowance mailed Jun. 9, 2015", 10 pgs.
"U.S. Appl. No. 13/837,294, Response filed Oct. 12, 2015 to Restriction Requirement mailed Aug. 24, 2015", 9 pgs.
"U.S. Appl. No. 13/837,294, Restriction Requirement mailed Aug. 24, 2015", 6 pgs.
"U.S. Appl. No. 13/837,774, Non Final Office Action mailed Sep. 18, 2015", 16 pgs.
"U.S. Appl. No. 13/837,774, Response filed Jul. 7, 2015 to Restriction Requirement mailed May 20, 2015", 10 pgs.
"U.S. Appl. No. 13/837,774, Restriction Requirement mailed May 20, 2015", 6 pgs.
"U.S. Appl. No. 14/833,385, Preliminary Amendment filed Aug. 25, 2015", 6 pgs.
"Chinese Application Serial No. 201380028572.4, Office Action mailed Aug. 13, 2015", (W/ English Translation), 16 pgs.
"Japanese Application Serial No. 2014-121515, Office Action mailed Jun. 2, 2015", (W/ English Translation), 10 pgs.

\* cited by examiner

SPACER BLOCK

TECHNICAL FIELD

The present disclosure relates to knee arthroplasty. More particularly, the present disclosure relates to an instrument for use during a knee arthroplasty procedure, and to a method for using the same.

BACKGROUND

In a total knee arthroplasty (TKA) procedure, a patient's distal femur is resected and replaced with a prosthetic femoral implant, and the patient's proximal tibia is resected and replaced with a prosthetic tibial implant. The prosthetic femoral implant articulates with the prosthetic tibial implant to restore joint motion.

Many factors influence joint motion after the TKA procedure. The size and shape of each prosthetic implant will impact joint motion. Additionally, the location and orientation of each prosthetic implant, which is determined by the location and orientation of the corresponding bone resections, will impact joint motion. The tension or laxity of the surrounding soft tissue will also impact joint motion. For example, if the surrounding collateral ligaments are too tense, joint motion may be limited, but if the surrounding collateral ligaments are too lax, improper femoral rotation or femoral lift-off may occur. Also, the soft tissue balance around the joint will impact joint motion.

Different surgical philosophies have traditionally influenced TKA instruments and procedures. For example, a first, "measured resection" philosophy emphasizes bone resections while preserving the natural joint axis and soft tissue. A second, "soft tissue balancing" philosophy emphasizes soft tissue modifications while preserving bone.

OVERVIEW

This overview is intended to provide an overview of subject matter of the present patent application. It is not intended to provide an exclusive or exhaustive explanation of the invention. The detailed description is included to provide further information about the present patent application.

The present patent application provides an exemplary TKA instrument and procedure. The instrument can separate the patient's tibia and femur, in both extension and flexion, to place the knee joint in tension and to measure a gap and an angle therebetween. The instrument can include various modular accessories. The accessories can provide flexibility of usage throughout the TKA procedure. For example, the instrument can be used before resecting or otherwise manipulating the patient's knee joint to evaluate the natural knee joint and plan the TKA procedure, as well as after resecting or otherwise manipulating the patient's knee joint to evaluate and/or further plan the TKA procedure. The accessories can also allow each individual user to select accessories that accommodate his or her own surgical philosophy and the needs of the particular patient. The accessories can also allow the user to incorporate multiple surgical philosophies into a single surgical procedure, such as by comparing the potential outcome of one accessory with the potential outcome of another accessory.

According to an example of the present disclosure, a knee arthroplasty instrument can be provided for use in a patient's knee joint, which includes a tibia and a femur. The instrument can include a spacer tool and a spacer shim. The spacer tool can include a tibial component configured for placement against the tibia and a femoral component configured for placement against the femur. The tibial component can be structured to accept a shim to place the patient's knee joint in tension by separating the tibia and the femur. The shim can be removably coupled to the spacer tool to increase the effective height of the tibial component.

According to an example of the present disclosure, a knee arthroplasty method for a patient's knee joint can include: estimating a resection gap, selecting one of a set of spacer shims, attaching the selected spacer shim to a tibial component, inserting an instrument with the spacer shim attached into the resection gap to separate the tibia and femur to verify a joint gap and a joint angle prior to implantation of an artificial joint.

To further illustrate the knee arthroplasty system and method disclosed herein, a non-limiting list of examples is provided here:

In Example 1, a knee arthroplasty system for use in a patient's knee joint can be provided that includes a spacer block instrument including a base portion, a tibial component extending from the base portion and configured for placement against a tibia, and a femoral component configured for placement against a femur, wherein the femoral component is rotatably coupled to the tibial component. The system further includes one or more spacer block shims structured for removable attachment to the tibial component.

In Example 2, the system of Example 1 is optionally configured such that each of the one or more spacer block shims comprises a spacer component and a handle portion, wherein the handle portion is structured to be positioned adjacent to the base portion of the spacer block instrument.

In Example 3, the system of any one of or any combination of Examples 1-2 is optionally configured such that the one or more spacer block shims comprises a plurality of spacer block shims, each of the spacer block shims defining a different shim height.

In Example 4, the system of Example 3 is optionally configured such that the shim height of each of the plurality of spacer block shims is between about 10 mm and about 13 mm.

In Example 5, the system of any one of or any combination of Examples 1-4 is optionally configured such that each of the one or more spacer block shims includes a connector structured to removably engage, in the alternative, the tibial component of the spacer block instrument.

In Example 6, the system of Example 5 is optionally configured such that the connector is a sliding joint.

In Example 7, the system of Example 6 is optionally configured such that the sliding joint is a dovetail joint.

In Example 8, the system of any one of or any combination of Examples 5-7 is optionally configured such that the connector includes a ball detent mechanism.

In Example 9, the system of any one of or any combination of Examples 1-8 is optionally configured such that the base portion of the spacer block instrument includes one or more channels extending through the base portion and configured to receive one or more alignment rods.

In Example 10, the system of Example 9 is optionally configured such that the handle portion of the one or more spacer block shims includes one or more channels configured to at least partially align with the one or more channels in the base portion of the spacer block instrument.

In Example 11, the system of any one of or any combination of Examples 2-10 is optionally configured such that the handle portion of the one or more spacer block shims includes a fin portion extending in a direction generally perpendicular to an axis of the spacer block instrument.

In Example 12, the system of Example 11 is optionally configured such that the fin portion is curved.

In Example 13, the system of any one of or any combination of Examples 1-12 is optionally configured to include a scale plate extending from the base portion and a pointer extending from the femoral component.

In Example 14, the system of Example 13 is optionally configured such that the scale plate includes an arcuate slot configured to at least partially receive the pointer, wherein the pointer travels within the arcuate slot as the femoral component rotates relative to the tibial component.

In Example 15, the system of any one of or any combination of Examples 13-14 is optionally configured such that the scale plate includes a numerical scale defining a range of joint angles.

In Example 16, a method of using a knee arthroplasty instrument to evaluate a resected knee joint can be employed that includes observing a resection gap between a distally resected femur and a proximally resected tibia, selecting a first spacer block shim from a plurality of spacer block shims, attaching the first spacer block shim to a tibial component of the knee arthroplasty instrument, and inserting the knee arthroplasty instrument into the resection gap, including positioning the tibial component and attached first spacer block shim adjacent to the proximally resected tibia and positioning a femoral component of the knee arthroplasty instrument adjacent to the distally resected femur, the femoral component being rotatable relative to the tibial component. The method further includes evaluating tension in the resected knee joint, including determining a first joint angle formed between the tibial component and the femoral component.

In Example 17, the method of Example 16 is optionally configured to include removing the knee arthroplasty instrument from the resection gap, detaching the first spacer block shim from the tibial component, selecting a second spacer block shim from the plurality of spacer block shims, attaching the second spacer block shim to the tibial component, reinserting the knee arthroplasty instrument into the resection gap, and evaluating tension in the resected knee joint, including determining a second joint angle formed between the tibial component and the femoral component, and comparing the first joint angle to the second joint angle.

In Example 18, the method of any one of or any combination of Examples 16-17 is optionally configured such that each of the plurality of spacer block shims defines a different shim height.

In Example 19, the method of any one of or any combination of Examples 16-18 is optionally configured such that determining a first joint angle comprises observing a scale plate extending from the knee arthroplasty instrument.

In Example 20, the method of Example 19 is optionally configured such that the scale plate includes an arcuate slot configured to at least partially receive a pointer extending from the femoral component.

In Example 21, the system or method of any one of or any combination of Examples 1-20 is optionally configured such that all elements or options recited are available to use or select from.

BRIEF DESCRIPTION OF THE DRAWINGS

In the drawings, like numerals can be used to describe similar elements throughout the several views. The drawings illustrate generally, by way of example, but not by way of limitation, various embodiments discussed in the present document.

DETAILED DESCRIPTION

Figure 1:
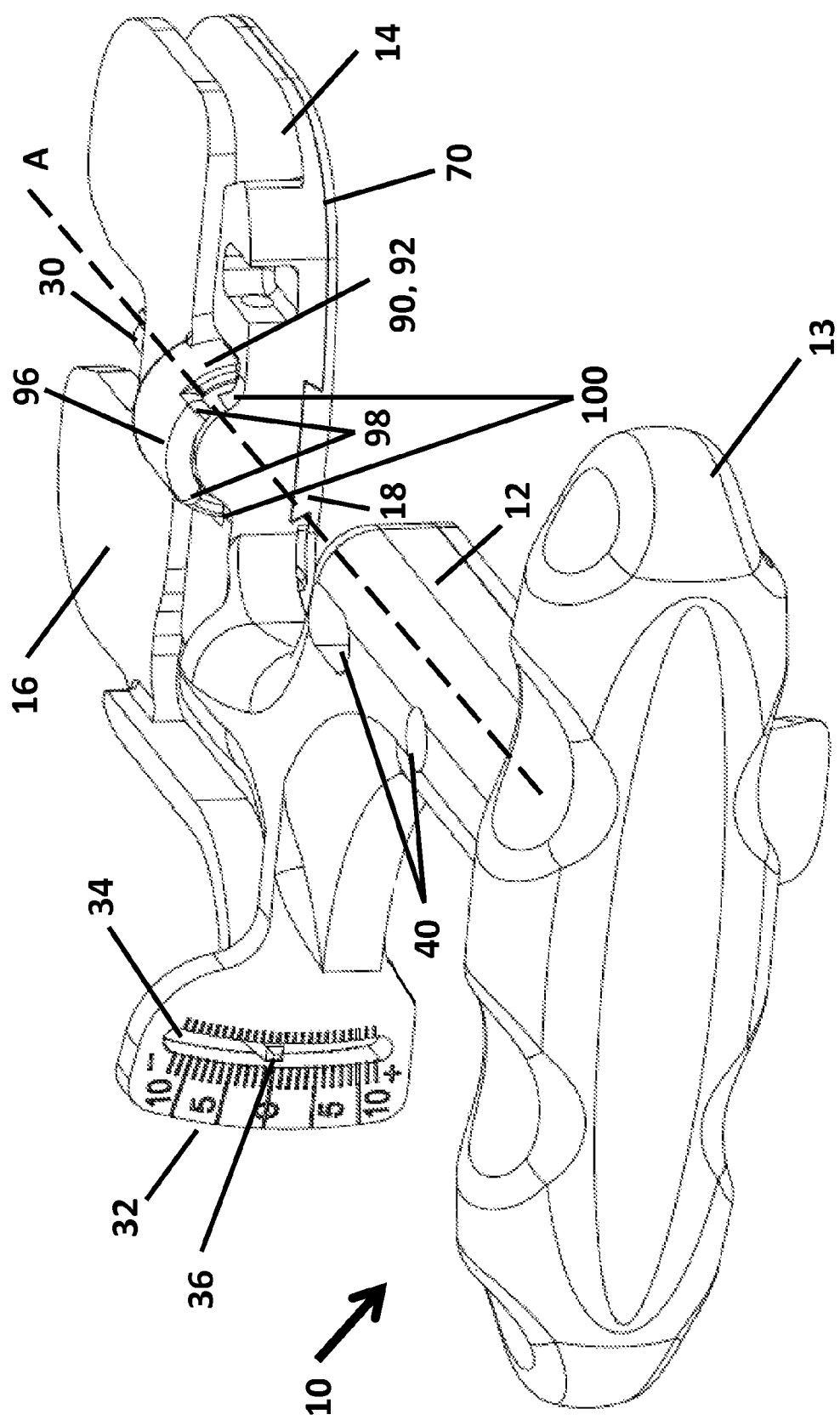
FIG. 1 is a perspective view of a knee arthroplasty instrument in accordance with an example of the present disclosure, the instrument including a base, a lower tibial component, an upper femoral component and a tibial spacer shim.
Figure 2:
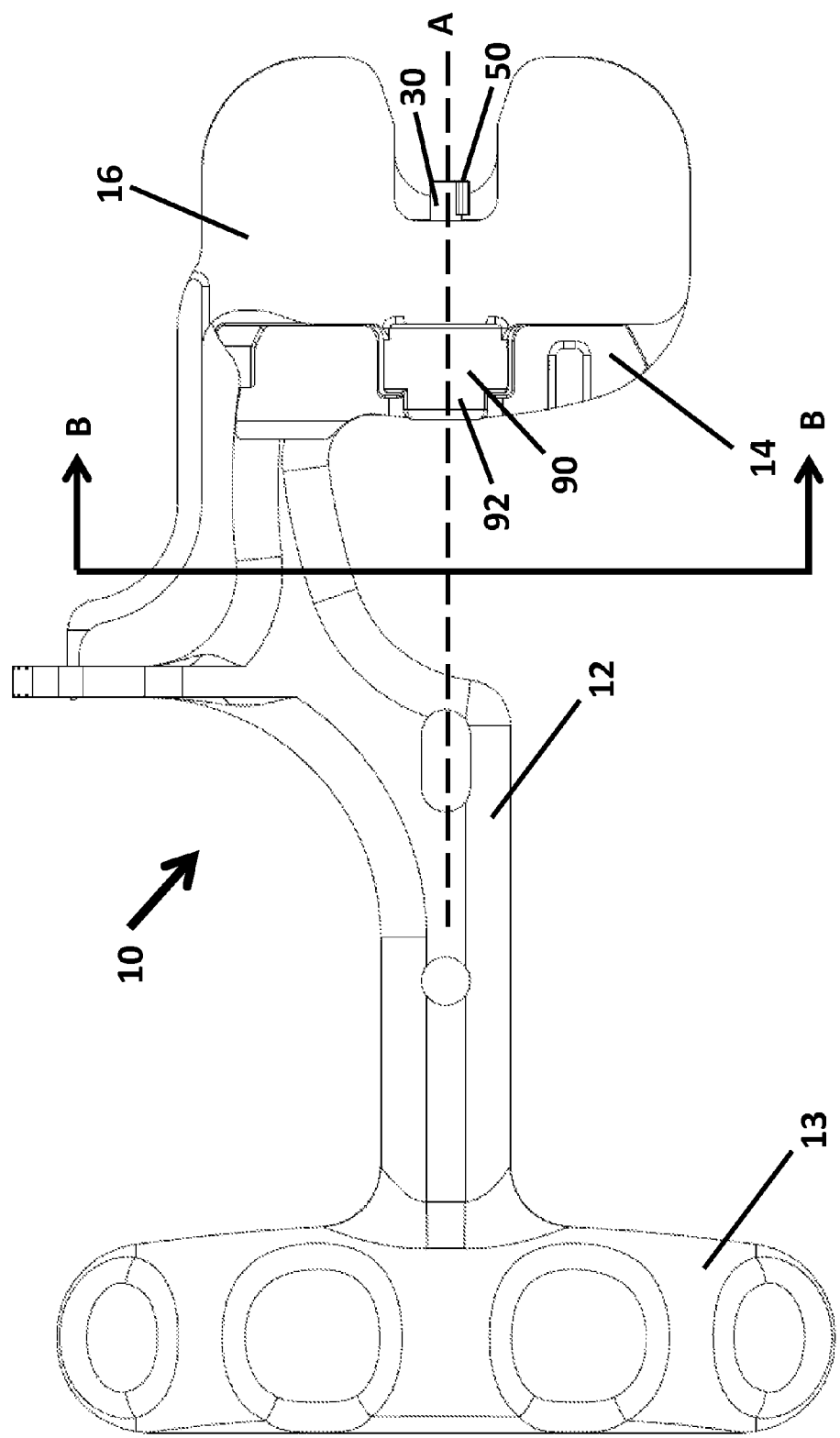
FIG. 2 is a top plan view of the instrument of FIG. 1, in accordance with an example of the present disclosure.

With reference to FIGS. 1 and 2, a spacer instrument 10 can be provided for separating a patient's tibia and femur and measuring a joint gap and a joint angle therebetween. Instrument 10 can include a base portion 12, a handle portion 13, a lower tibial component 14, an upper femoral component 16, a post 30 configured to couple femoral component 16 to tibial component 14, and a tibial spacer block shim 18. Base portion 12 can include one or more channels 40 extending at least partially therethrough and oriented generally perpendicular to a plane formed by tibial component 14 to allow for the use of one or more alignment rods in cooperation with instrument 10. As will be discussed in further detail below, femoral component 16 and spacer block shim 18 can be removably attached to tibial component 14 using a suitable connection means. Tibial component 14, femoral component 16 and spacer block shim 18 (see FIG. 1) can be offset from base portion 12, as shown in FIG. 2, to accommodate the patient's patella.

Femoral component 16 can be configured to rotate relative to tibial component 14. More specifically, femoral component 16 can be configured to rotate relative to tibial component 14 about rotation axis A. As shown in FIG. 2, post 30 can engage with femoral component 16 at one or more locations along rotation axis A, and femoral component 16 can be configured to rotate about post 30. In an example, the rotation axis A of femoral component 16 can be parallel to the longest dimension of the base portion 12, such as a longitudinal dimension extending between a proximal end and a distal end of base portion 12.

An angle measuring means can be provided to measure an angle α between tibial component 14 and femoral component 16 about the rotation axis A. In an example, as illustrated in FIG. 1, the angle measuring means can include a scale plate 32 extending from base portion 12. As further illustrated in FIG. 1, scale plate 32 can define an arcuate slot 34 configured to receive a pointer 36 extending from femoral component 16. As femoral component 16 rotates relative to base portion 12 about axis A, pointer 36 can be configured to move along or through arcuate slot 34 of scale plate 32. The angle α between tibial component 14 and femoral component 16 can be determined by reading the value from scale plate 32 that is adjacent to pointer 36. When femoral component 16 is oriented parallel to tibial component 14, pointer 36 can be centered in slot 34 corresponding to an angle α of 0 degrees. As femoral component 16 deviates from this parallel orientation, pointer 36 can move along slot 34 to a positive angle α greater than 0 degrees or a negative angle α less than 0 degrees. As discussed in further detail below, angle α can indicate a varus/valgus angle of the patient's knee joint and/or internal/external rotation of the patient's knee joint.

Figure 3:
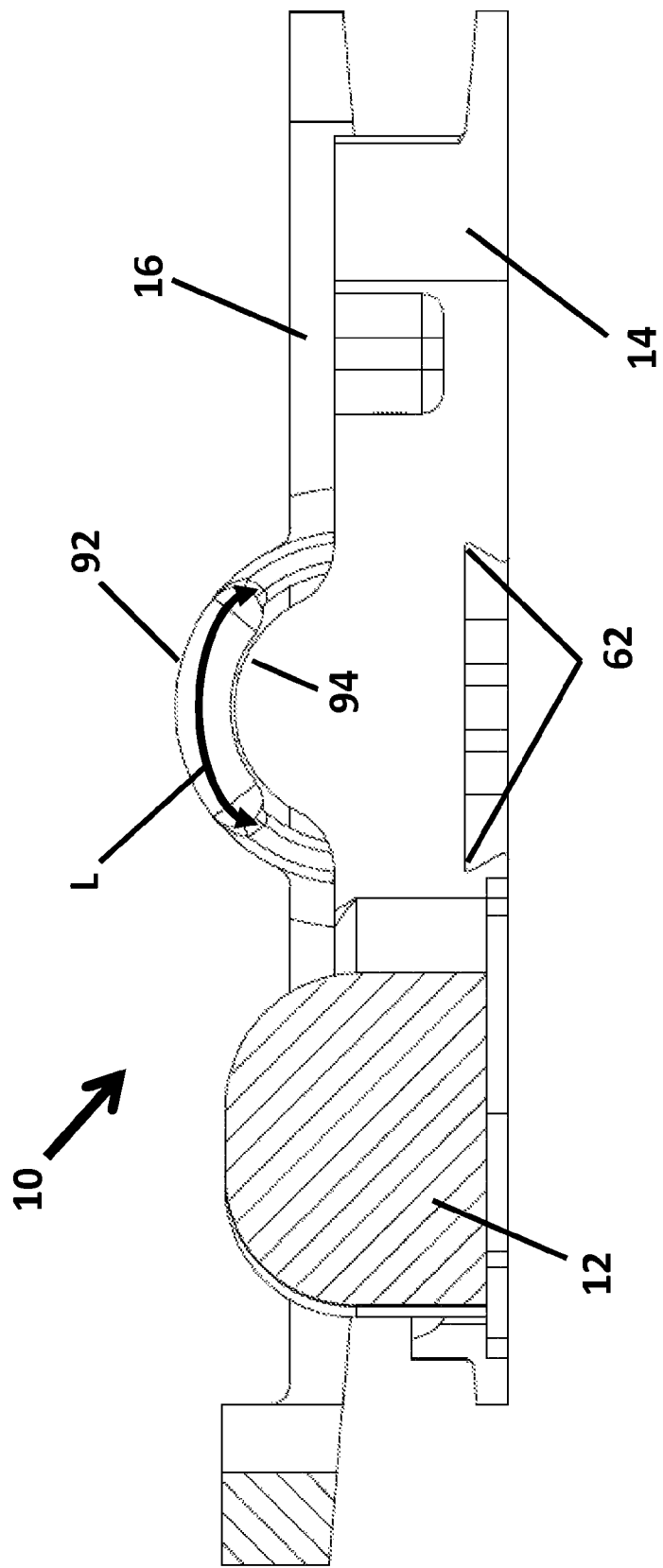
FIG. 3 is a cross-sectional view of a portion of the instrument taken along line B-B of FIG. 2, in accordance with an example of the present disclosure.

An angle rotation limiting means can be provided to restrict the angle of motion between tibial component 14 and femoral component 16 about rotation axis A. Referring to FIG. 1, femoral component 16 can include a femoral cover 90 with an outer surface 92 and an inner surface 94 (see FIG. 3) that includes a rotation restriction portion 96 with one or more rotation restriction surfaces 98. In an example, outer surface 92 and inner surface 94 can be located on circular arcs centered about axis A so that rotation of femoral component 16 about post 30 can result in similar rotation of femoral cover 90 about axis A. Tibial component 14 can include one or more restriction pocket surfaces 100. In an example, as femoral component 16 rotates about post 30, the rotation angle α between tibial component 14 and femoral component 16 can be limited by the interference of a restriction surface 98 with a pocket surface 100. As shown in FIG. 3, which is a cross-sectional view of a portion of instrument 10 taken along line B-B of FIG. 2, rotation angle α of femoral component 16 can depend on the arc length L of rotation restriction portion 96.

Instrument 10 can include a set of modular accessories, examples of which are described further below. Instrument 10 and the accessories can be provided together as a system. In this manner, a surgeon or another user can select a first accessory from the system and attach that first accessory to instrument 10. As the surgical procedure progresses, the surgeon can select a second accessory from the system and attach the second accessory to instrument 10. In various examples, the first accessory can be left in place when the second accessory is attached to instrument 10. In other examples, the first accessory can be removed from instrument 10 to accommodate the second accessory. A variety of different coupling mechanisms (e.g., dovetail joints) and locking mechanisms (e.g., keys, ball detents) can be used to selectively receive and retain the desired modular accessory on instrument 10. Additional information regarding modular accessories for instrument 10 can be found in PCT Publication No. WO2013013094 to Claypool et al., entitled "Knee Arthroplasty Instrument," the disclosure of which is incorporated herein by reference in its entirety.

Figure 4:
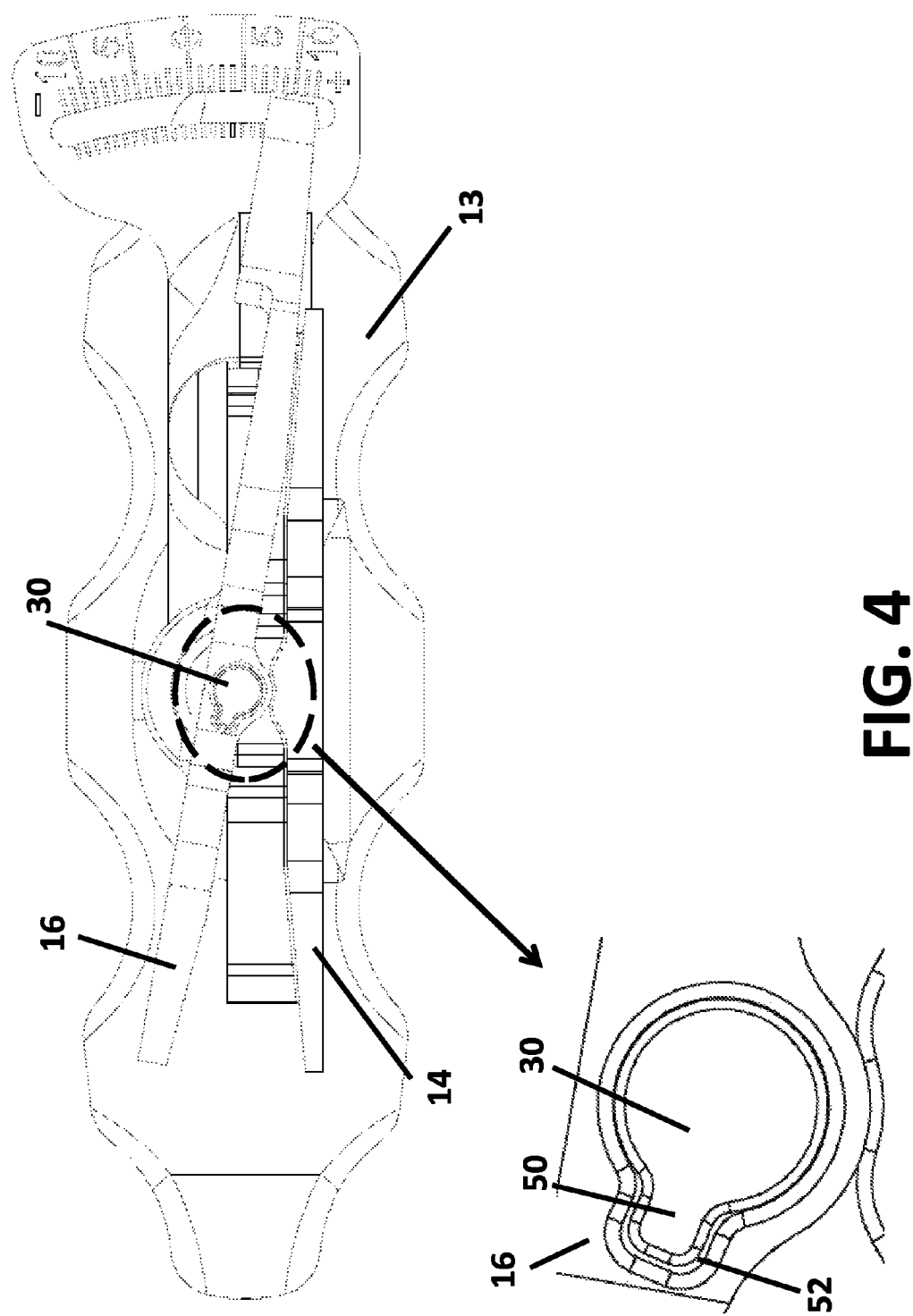
FIG. 4 is a distal end view of the instrument detailing alignment of key and keyway features, in accordance with an example of the present disclosure.

FIG. 4 is a distal end view of instrument 10 detailing attachment of femoral component 16, which can be considered a modular accessory that can be removably coupled to instrument 10. In an example, a key 50 can be located on post 30 and a keyway 52 can be located in femoral component 16 as shown in FIG. 4. Alignment of keyway 52 with key 50 can allow a surgeon to slide keyway 52 over key 50 along axis A in a direction toward handle 13 until key 50 extends at least partially through femoral component 16 (see FIG. 2) thereby locating femoral component 16 onto post 30 and allowing femoral component 16 to rotate freely about post 30.

Figure 5:
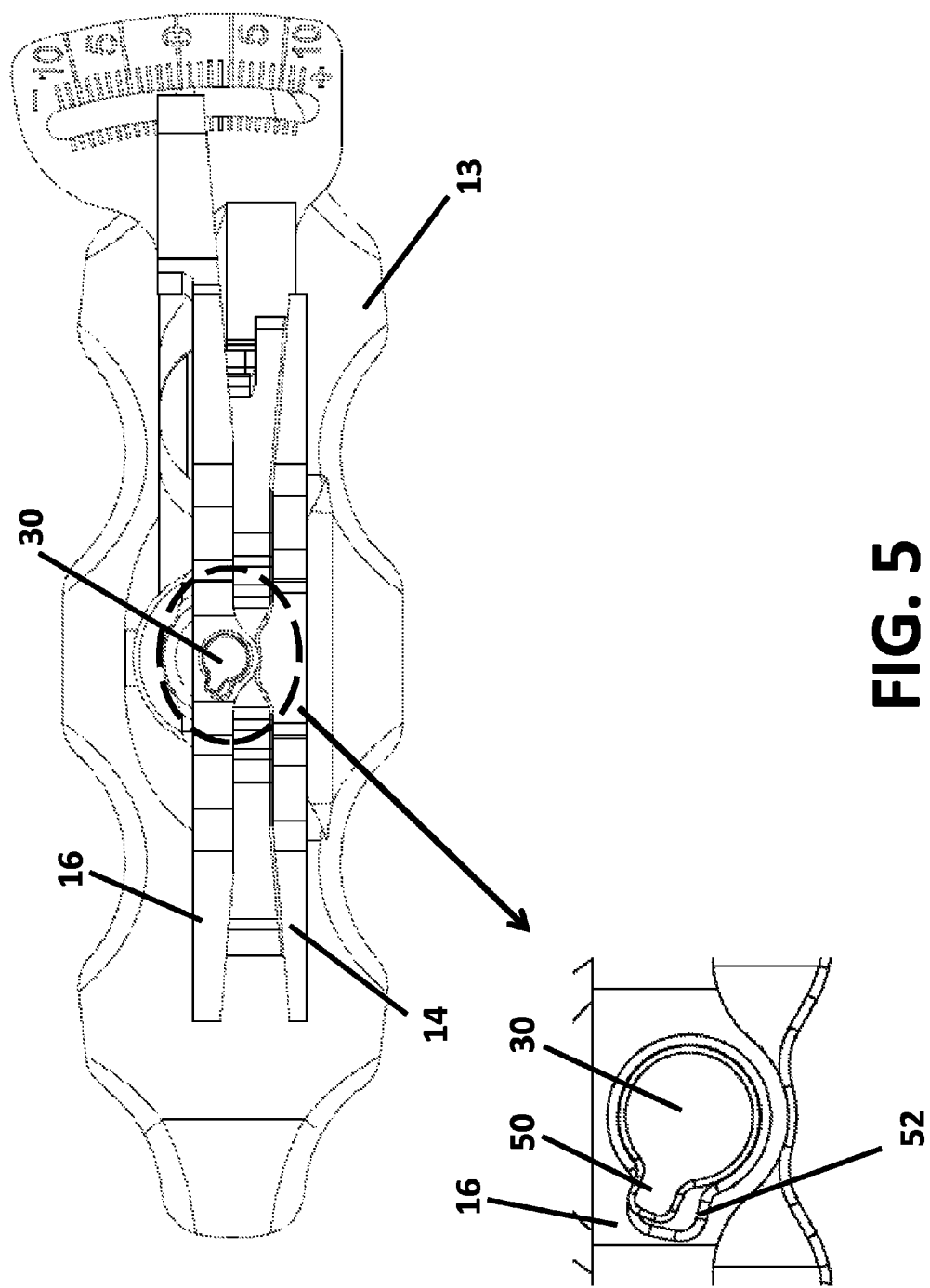
FIG. 5 is a distal end view of the instrument detailing an offset of the key and keyway features, in accordance with an example of the present disclosure.

FIG. 5 is a distal end view of instrument 10 detailing an offset of the key 50 and keyway 52 features. As shown in FIG. 5, keyway 52 ordinarily remains offset from key 50 during rotation of femoral component 16 about post 30 so as to interfere with the motion of femoral component 16 along axis A, thereby preventing detachment of femoral component 16 from instrument 10 during use. Removal of femoral component 16 can be effected by rotating femoral component 16 about post 30 until keyway 52 is once again aligned with key 50 (see FIG. 4), allowing a surgeon to slide femoral component 16 along axis A in a direction away from handle 13 for removal over post 30.

Figure 6:
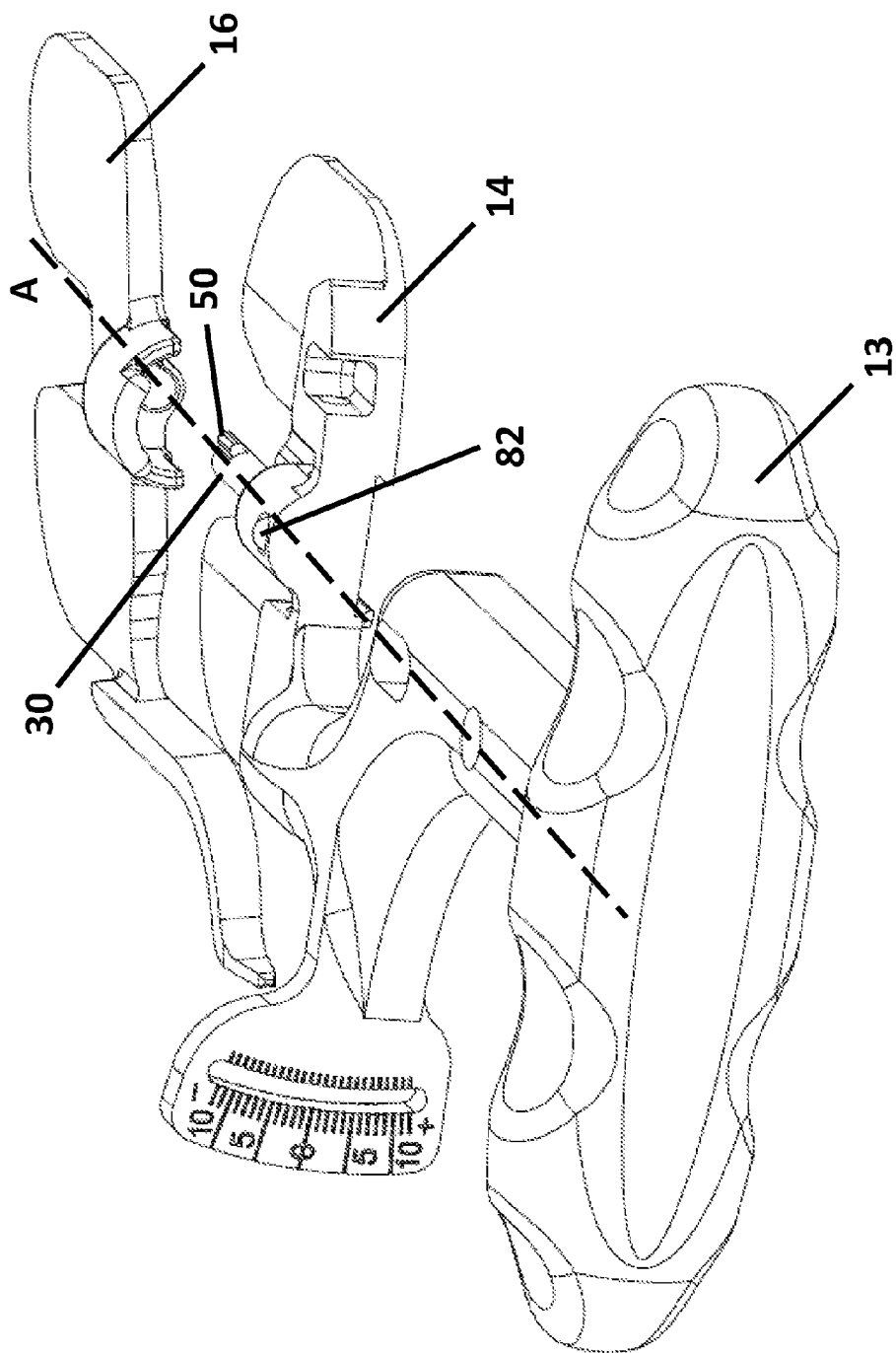
FIG. 6 is an exploded perspective view of the instrument showing an example of a spring-loaded ball plunger attached to the lower tibial component, in accordance with an example of the present disclosure.
Figure 7:
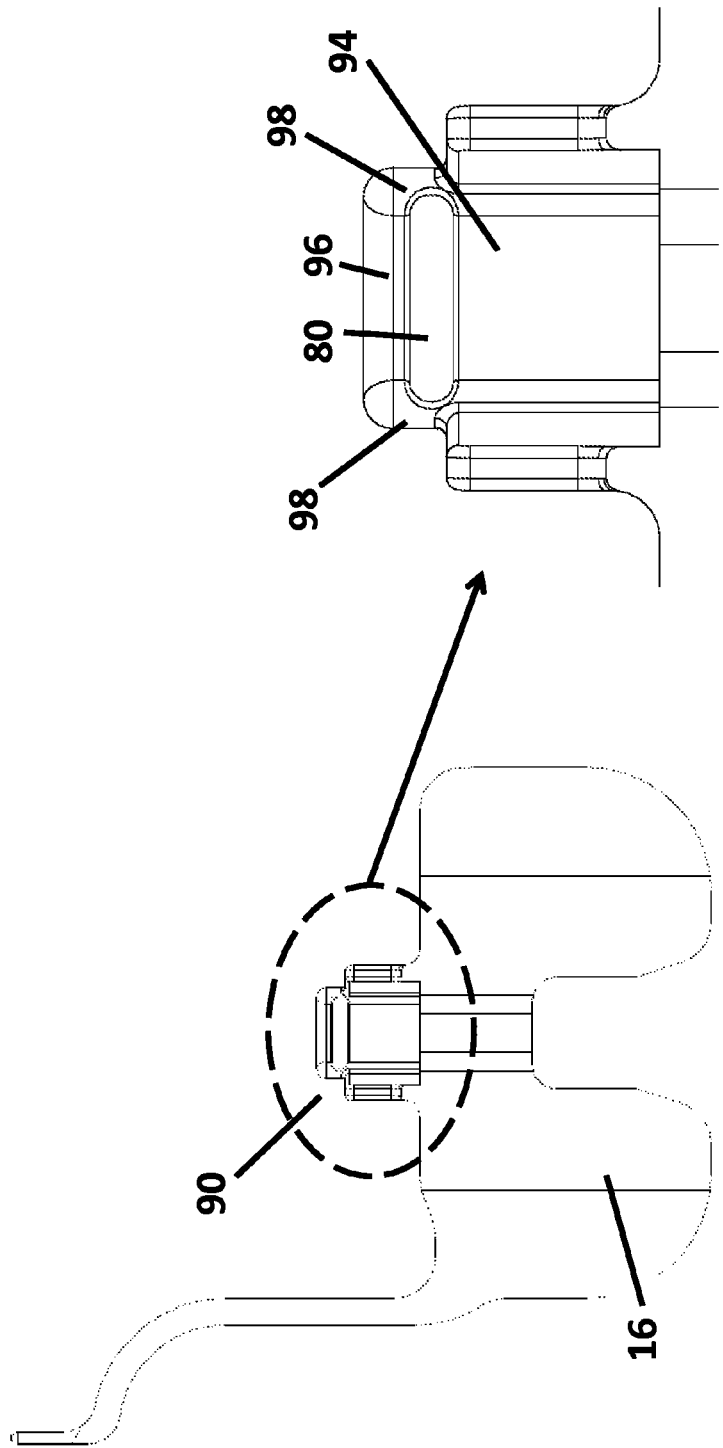
FIG. 7 is a bottom view of the upper femoral component showing an example of a detent channel, in accordance with an example of the present disclosure.

FIG. 6 is an exploded perspective view of instrument 10 illustrating femoral component 16 detached from tibial component 14. FIG. 7 is a bottom view of femoral component 16 after removal from instrument 10. Together, FIGS. 6 and 7 depict exemplary features that can allow femoral component 16 to be removably coupled to tibial component 14.

In an example, instrument 10 can include a ball detent mechanism to removably couple femoral component 16 to tibial component 14. A ball detent mechanism can include, but is not limited to, a spring-loaded ball plunger component in combination with a cavity located on an adjacent component. In an example, tibial component 14 can include a spring-loaded ball plunger 82 as shown in FIG. 6 and femoral component 16 can include a detent channel 80 located on inner surface 94 of femoral cover 90 as shown in FIG. 7. With reference to FIGS. 6 and 7, femoral component 16 can be removably coupled to tibial component 14 by sliding femoral component 16 over post 30 along axis A toward handle 13 whereby the spring biasing force of spring-loaded ball plunger 82 engages detent channel 80 so that motion of femoral component 16 along axis A can be impeded. Femoral component 16 can thereafter be removed from tibial component 14 by applying an axial force to femoral component 16 along axis A in a direction away from handle 13 to overcome the spring biasing force applied by spring-loaded ball plunger 82 to channel 80, thereby releasing femoral component 16 for sliding removal over post 30.

Figure 8:
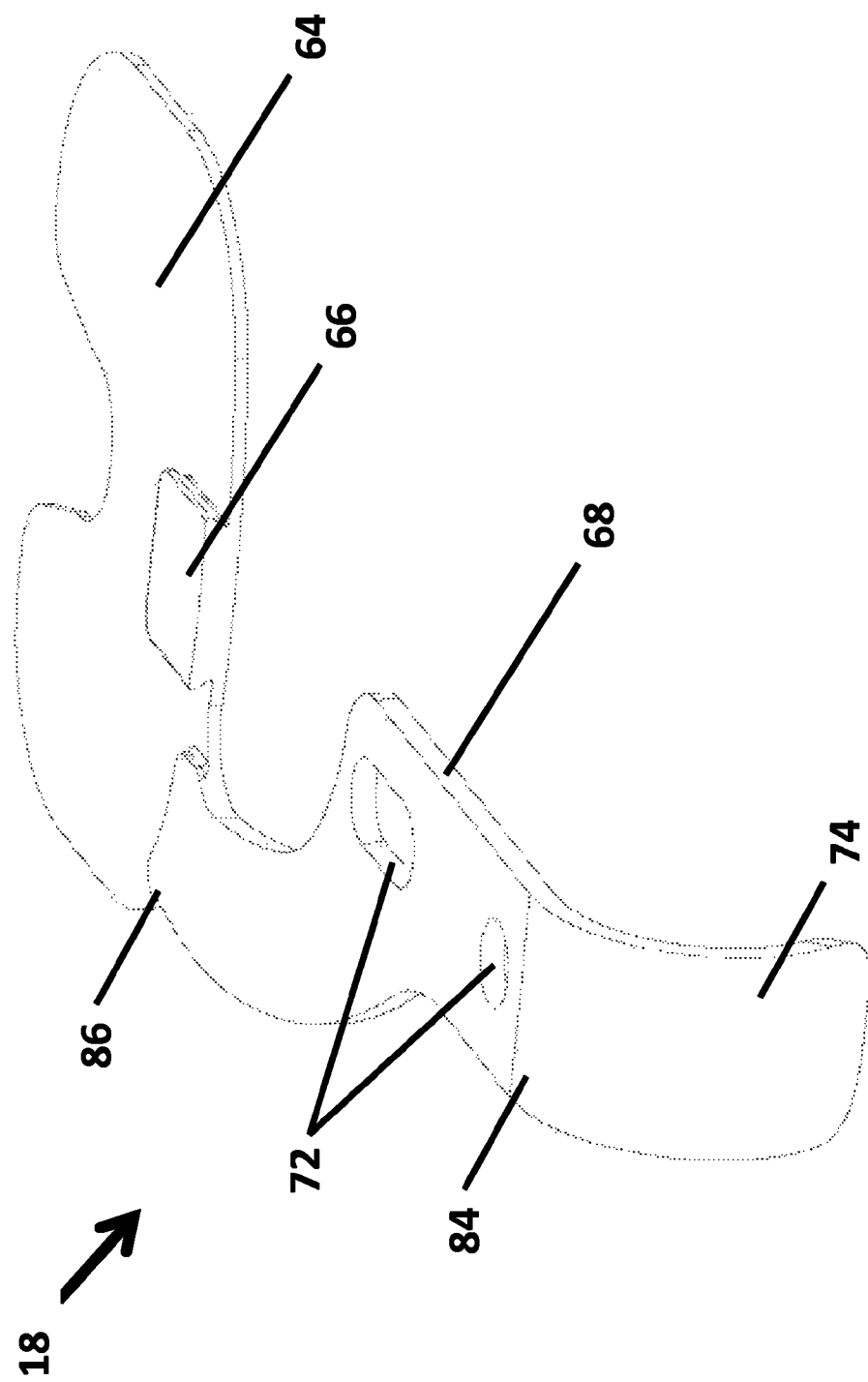
FIG. 8 is a perspective view of the tibial spacer shim of FIG. 1, in accordance with an example of the present disclosure.

FIG. 8 is a perspective view of spacer block shim 18 removed from instrument 10. In an example, spacer block shim 18 can also be considered a modular accessory that can be removably coupled to instrument 10 In use, spacer block shim 18 can be removably coupled to tibial component 14 thereby increasing the overall effective thickness of tibial component 14. Spacer block shim 18 can be coupled to tibial component 14 to perform various functions, such as to adjust tension of soft tissue in the knee. Spacer block shim 18 can include a spacer component 64, a connector 66, and a shim handle portion 68 with a distal end 84 and a proximal end 86. As illustrated in FIG. 8, spacer component 64 can be configured to extend from proximal end 86. In an example, spacer component 64 can be substantially of the same size and shape as tibial component 14. However, in various examples, spacer component 64 can be provided in different shapes, sizes and thicknesses to vary the overall effective thickness of tibial component 14. Thus, in an example, a plurality of spacer block shims 18 having spacer components 64 with different thicknesses can be provided for selection by the surgeon or user.

Shim handle portion 68 can be structured for placement adjacent to a tibial side 70 of base portion 12 (see FIG. 1). In an example, shim handle portion 68 can be configured with the same general shape as tibial side 70 of base portion 12. However, shim handle portion 68 can assume any suitable shape. Shim handle portion 68 can include one or more channels 72 that can align with the one or more channels 40 of base portion 12 to allow for the use of one or more alignment rods in cooperation with instrument 10. As illustrated in FIG. 8, shim handle portion 68 can include a fin portion 74 that can extend away from a plane formed by shim handle portion 68 and away from tibial side 70 of base portion 12. In an example, fin portion 74 can be of a curved construction as shown in FIG. 8, and can extend generally perpendicular to the plane formed by shim handle portion 68. However, fin portion 74 can be provided in different shapes, sizes, thicknesses and locations along shim handle portion 68.

Figure 9:
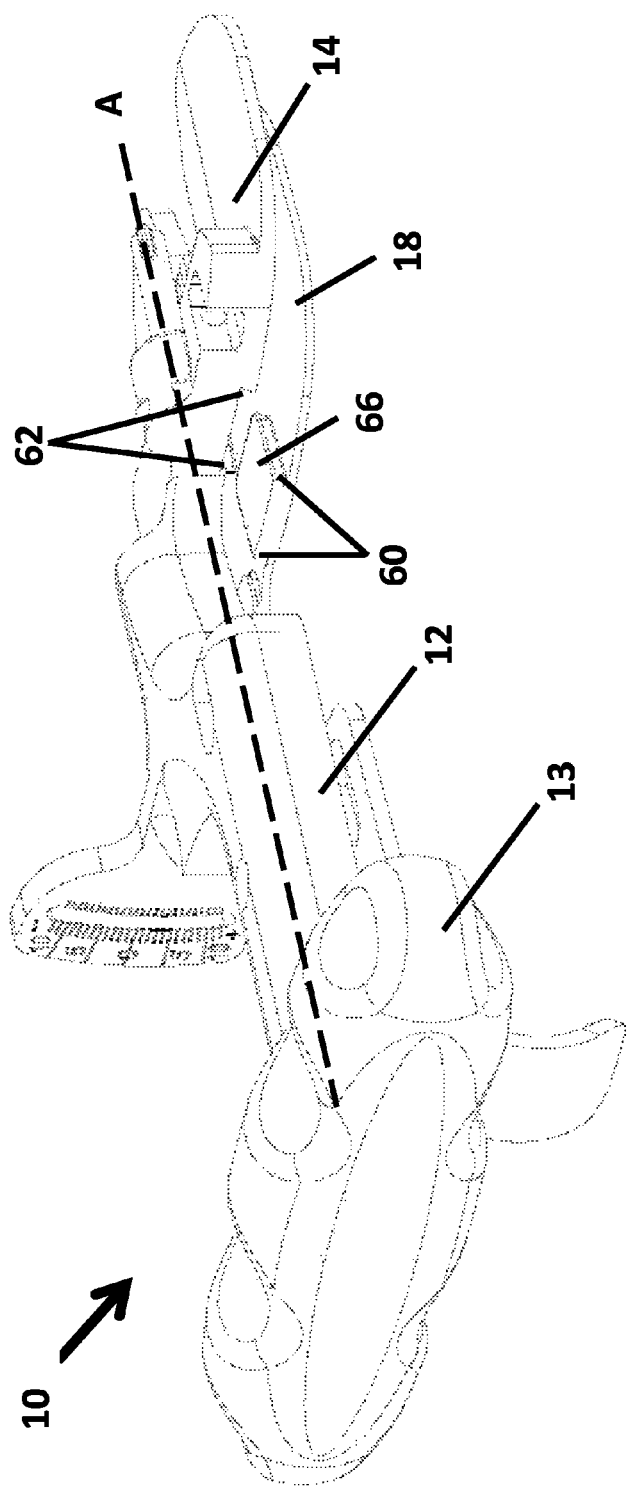
FIG. 9 is a perspective view illustrating the removable attachment of the tibial spacer shim to the instrument of FIG. 1, in accordance with an example of the present disclosure.

Spacer block shim 18 can include any suitable means that allow spacer block shim 18 to be removably coupled to tibial component 14 of instrument 10, such as coupling means that allow spacer block shim 18 to slide linearly relative to tibial component 14 during engagement. In FIG. 9, for example, spacer block shim 18 can be removably coupled to tibial component 14 by a sliding engagement via one or more tongues 60 of connector 66 and one or more corresponding grooves 62 of tibial component 14, where tongues 60 on connector 66 are sized to slide into the corresponding grooves 62 in tibial component 14 along axis A. In another example, the sliding engagement of spacer block shim 18 and tibial component 14 can alternatively or additionally utilize a ball detent mechanism between spacer block shim 18 and tibial component 14. The ball detent mechanism can include features similar to the spring-loaded ball plunger 82 and the detent channel 80 previously described.

An exemplary method of using instrument 10 will now be described with reference to FIGS. 10-13. The order of the following steps can vary depending on factors such as the surgeon's preference, the patient's bone quality, the state of the patient's surrounding soft tissue, and the types of prosthetic implants being used.

First, the surgeon can perform pre-operative planning. The planning step can involve taking X-rays or other images of the patient's knee joint 200 and selecting prosthetic implants to accommodate the patient's needs, for example.

Figure 10:
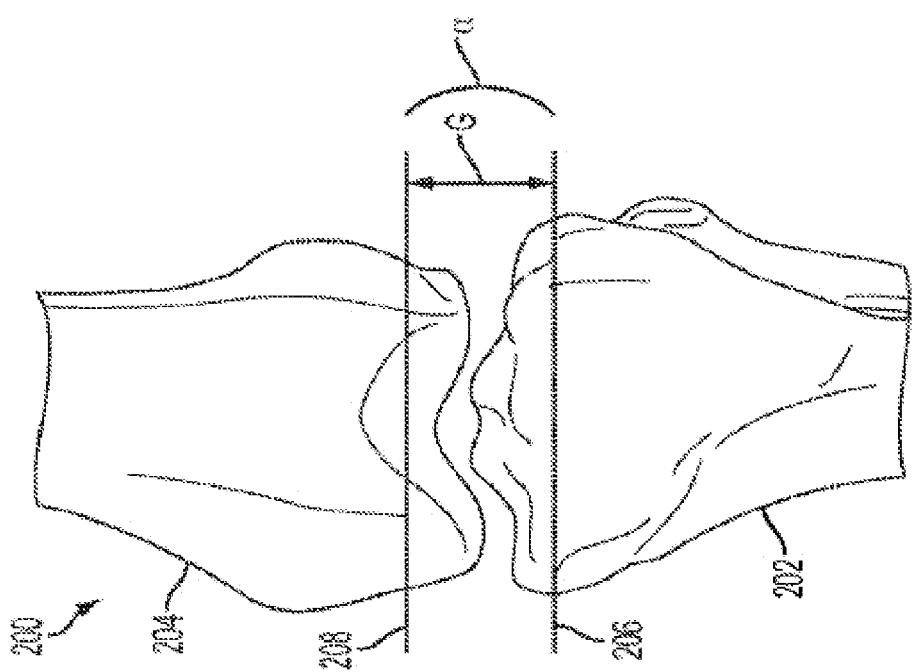
FIG. 10 is an anterior elevational view of a knee joint in extension, in accordance with an example of the present disclosure.
Figure 11:
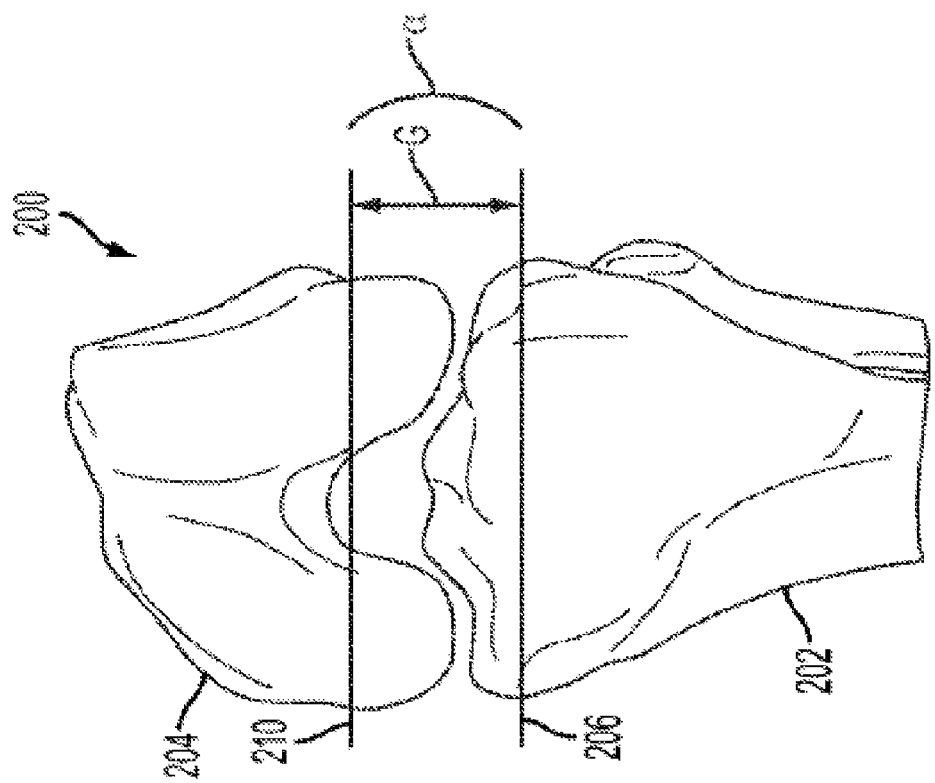
FIG. 11 is an anterior elevational view of the knee joint in flexion, in accordance with an example of the present disclosure.

Next, as shown in FIGS. 10 and 11, the surgeon can expose tibia 202 and femur 204 of the patient's knee joint 200. The exposing step can involve incising the patient's skin, incising the patient's joint capsule, and removing osteophytes, for example.

With the patient's knee joint 200 now exposed, the surgeon can use instrument 10 to separate tibia 202 and femur 204 of the patient's knee joint 200 to a predetermined tension, and to plan and identify the desired bone resections of tibia 202 and femur 204. With the patient's knee joint 200 tensioned in extension (FIG. 10), the surgeon can plan and identify a proximal tibial resection 206 and a distal femoral resection 208 that will produce a desired gap G and angle α therebetween. The extension angle α can be referred to as a varus/valgus angle. With the patient's knee joint 200 tensioned in flexion (FIG. 11), the surgeon is able to plan and identify the proximal tibial resection 206 and a posterior femoral resection 210 that will produce a desired gap G and angle α therebetween. The flexion angle α can be referred to as an internal/external rotation angle. Gap G and angle α between tibia 202 and femur 204 can be selected based on the patient's age, the patient's bone quality, the state of the patient's surrounding soft tissue, the types of prosthetic implants being used, and other factors, for example.

Tibia 202 and femur 204 can be resected using suitable cut guides. For example, the Minimally Invasive Surgery (MIS) Tibial Cut Guide Assembly, which is available from Zimmer, Inc. of Warsaw, Ind., can be used to form the proximal tibial resection 206 in tibia 202. Suitable cut guides can also be used to form the distal femoral resection 208 and the posterior femoral resection 210 in femur 204.

In addition to evaluating bone resections, the surgeon can also evaluate soft tissue resections, releases, or other soft tissue operations that would impact gap G and angle α between tibia 202 and femur 204. For example, if the surgeon desires a balanced angle α of 0 degrees between tibia 202 and femur 204, the surgeon can release or otherwise relax ligaments on one side of the patient's knee joint 200 (e.g., the medial side) relative to the opposing side of the patient's knee joint 200 (e.g., the lateral side). As another example, if the surgeon desires a larger gap G between tibia 202 and femur 204 without resecting additional bone from tibia 202 or femur 204, the surgeon can release or otherwise relax ligaments around the patient's knee joint 200.

According to an example of the present disclosure, knee joint 200 can be prepared such that gap G and angle α between tibia 202 and femur 204 are the same or substantially the same in extension (FIG. 10) as in flexion (FIG. 11). In this example, a three-dimensional space can be maintained between tibia 202 and femur 204 in extension and flexion. For example, a surgeon implanting a prosthetic femoral implant having equally thick distal and femoral condyles can prepare an extension gap G that is the same as the flexion gap G, while a surgeon implanting a prosthetic femoral implant having distal and femoral condyles of different thicknesses can prepare an extension gap G that varies the flexion gap G to account for the different thicknesses. When angle α is 0 degrees, such that the proximal tibial resection 206 is parallel to the distal femoral resection 208 in extension (FIG. 10) and the posterior femoral resection 210 in flexion (FIG. 11), the three-dimensional space between tibia 202 and femur 204 will be substantially rectangular in shape in extension and flexion. It is also within the scope of the present disclosure that the surgeon may tolerate differences between the extension angle α (FIG. 10) and the flexion angle α (FIG. 11), such as differences of 1 degree, 2 degrees, 3 degrees or more.

In view of the foregoing, instrument 10 can be used to measure the natural gap G and angle α between tibia 202 and femur 204 in extension and flexion, and to plan or identify the proximal tibial resection 206, the distal femoral resection 208, the posterior femoral resection 210, and/or any soft tissue resections that will produce a desired gap G and angle α between tibia 202 and femur 204 in extension and flexion. Additionally, after resecting or otherwise manipulating knee joint 200, instrument 10 can be used to verify the desired gap G and angle α between tibia 202 and femur 204 in extension and flexion. Therefore, instrument 10 can be used before and/or after resecting or otherwise manipulating knee joint 200.

Figure 12:
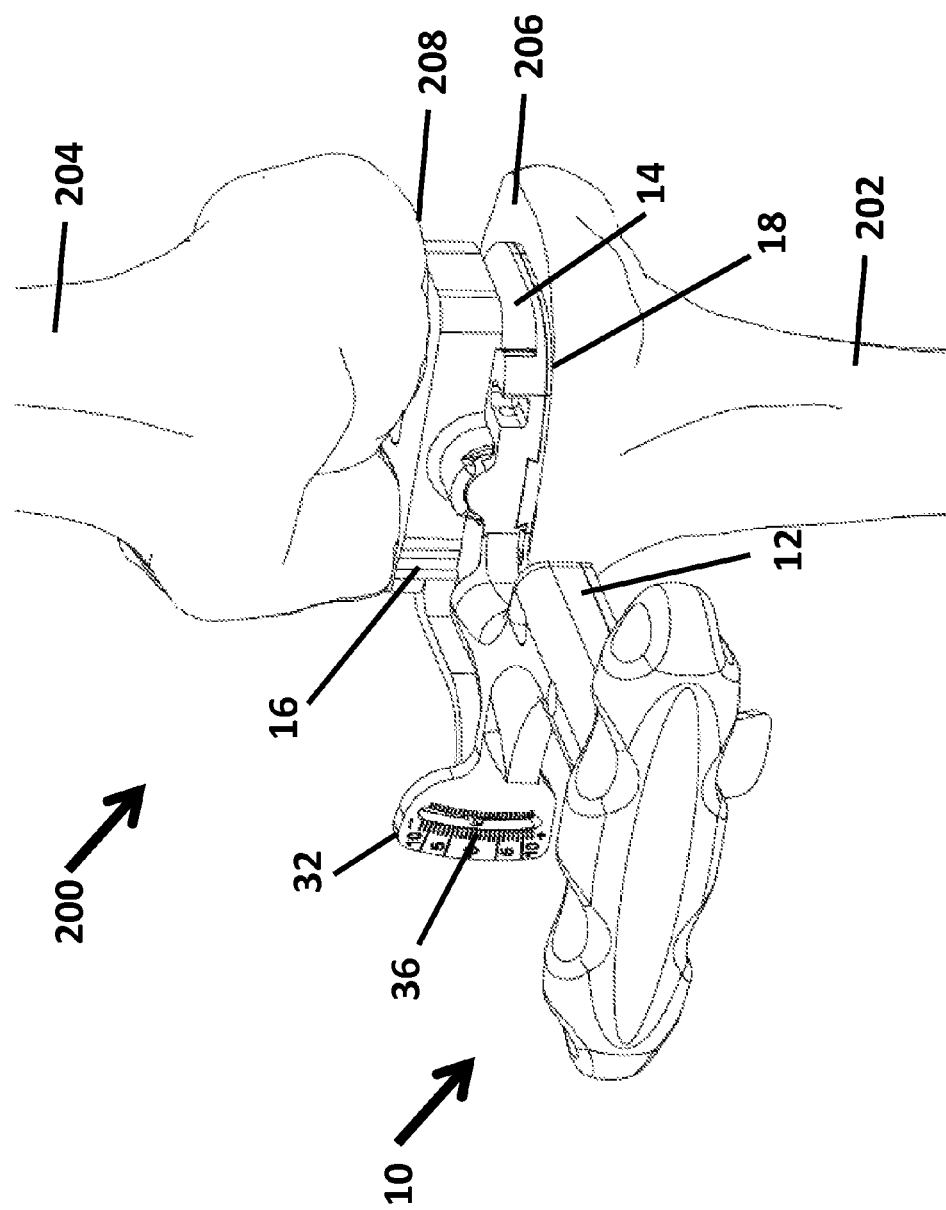
FIG. 12 is a perspective view of the instrument of FIG. 1 with the tibial spacer shim positioned within the knee joint in extension, in accordance with an example of the present disclosure.
Figure 13:
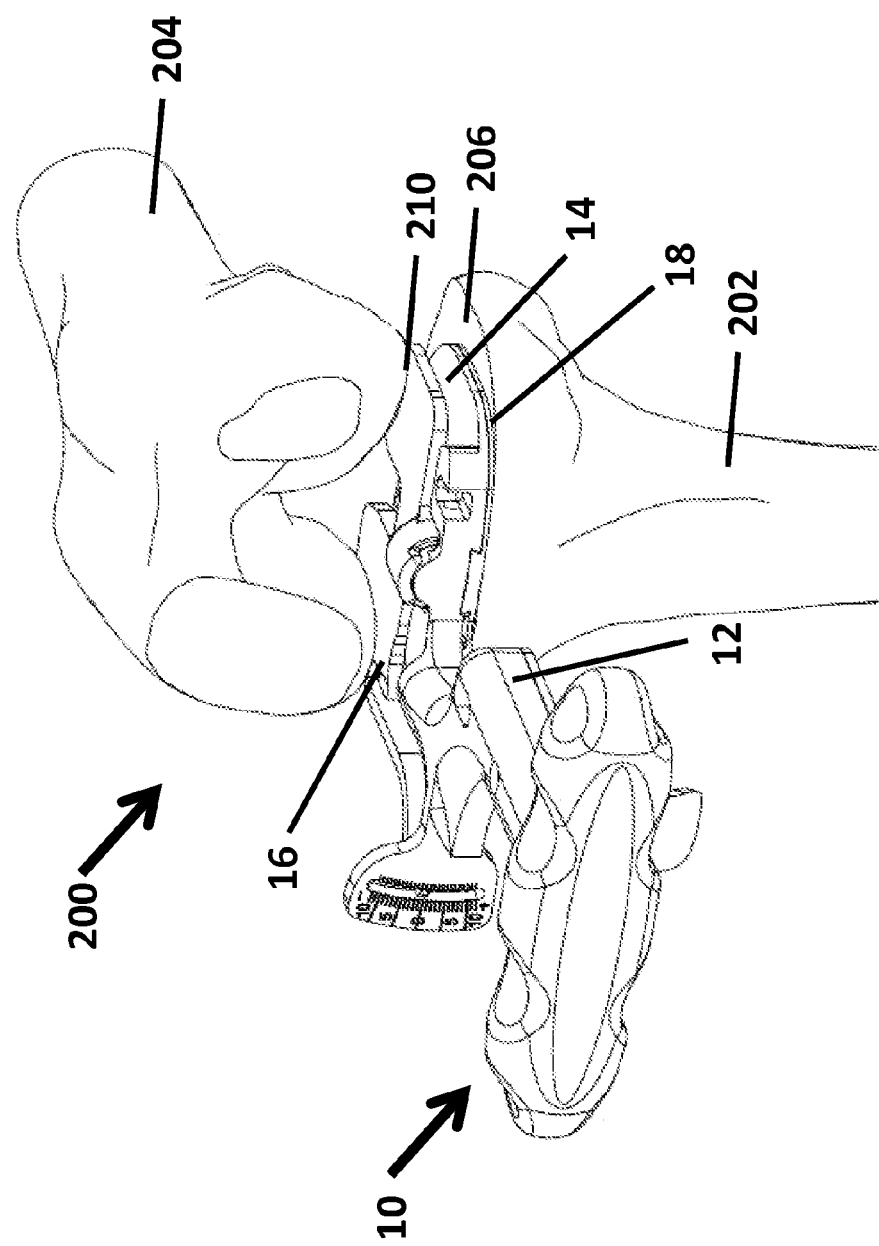
FIG. 13 is a perspective view of the instrument of FIG. 1 with the tibial spacer shim positioned within the knee joint in flexion, in accordance with an example of the present disclosure.

The use of instrument 10 to measure gap G and angle α between tibia 202 and femur 204 is described further with reference to FIGS. 12 and 13, for example. In FIG. 12, instrument 10 is illustrated as being used with the patient's knee joint 200 in extension. Proximal tibial resection 206 has already been formed in tibia 202, and distal femoral resection 208 has already been formed in femur 204. Thus, in the illustrated example of FIG. 12, instrument 10 is being used to verify the resected gap G and the resected angle α between tibia 202 and femur 204. A first spacer block shim 18 can be removably coupled to tibial component 14 of instrument 10 so that first spacer block shim 18 contacts the resected tibial surface when the instrument 10 is inserted into the resection gap G. The first spacer block shim 18 can be preselected with knowledge of the resected gap G to verify the desired resected gap G and resected angle α have been achieved. After attaching first spacer block shim 18 to instrument 10, first spacer block shim 18 can be placed against proximal tibial resection 206. Femoral component 16 can be coupled through post 30 to tibial component 14 and placed against distal femoral resection 208. With tibial component 14 and femoral component 16 of instrument 10 positioned to separate tibia 202 and femur 204, the surgeon can check the extension gap G between proximal tibial resection 206 and distal femoral resection 208. Also, the surgeon can measure the extension angle between proximal tibial resection 206 and distal femoral resection 208 by referencing scale plate 32 on base portion 12 and pointer 36 on femoral component 16.

Where the resulting tension in the knee is deemed to be insufficient, instrument 10 can be removed from the resection gap G, first spacer block shim 18 can be removed from instrument 10 and a second spacer block shim that is incrementally larger than first spacer block shim 18 can be removably attached to instrument 10. Thereafter, instrument 10 can be reinserted into the resection gap G as described previously. Where the resulting tension in the knee is deemed to be excessive, instrument 10 can be removed from the resection gap G, first spacer block shim 18 can be removed from instrument 10 and a second spacer block shim that is incrementally smaller than first spacer block shim 18 can be removably attached to instrument 10 and thereafter reinserted in the resection gap G as previously described.

In FIG. 13, instrument 10 is illustrated as being used with the patient's knee joint 200 in flexion. Proximal tibial resection 206 has already been formed in tibia 202, and posterior femoral resection 210 has already been formed in femur 204. Thus, as shown in FIG. 13, instrument 10 is being used to verify the resected gap G and the resected angle α between tibia 202 and femur 204. A first spacer block shim 18 of instrument 10 can be placed against proximal tibial resection 206. Femoral component 16 can be coupled through post 30 to tibial component 14 of instrument 10 and placed against posterior femoral resection 210. With first spacer block shim 18 and femoral component 16 of instrument 10 positioned to separate tibia 202 and femur 204, the surgeon can verify that the flexion gap G of FIG. 13 is the same as or substantially the same as the extension gap G of FIG. 12. Also, the surgeon can verify that the flexion angle α of FIG. 13 is the same as or substantially the same as the extension angle α of FIG. 12. Although FIGS. 12 and 13 only show distal femoral resection 208 and posterior femoral resection 210 in femur 204, other resections (e.g., chamfer cuts and an anterior cut) may also exist in femur 204 when instrument 10 is in use.

Where the resulting tension in the knee is deemed to be insufficient, instrument 10 can be removed from the resection gap G, first spacer block shim 18 can be removed from instrument 10 and a second spacer block shim that is incrementally larger than first spacer block shim 18 can be removably attached to instrument 10. Thereafter, instrument 10 can be reinserted into the resection gap G as described previously. Where the resulting tension in the knee is deemed to be excessive, instrument 10 can be removed from the resection gap G, first spacer block shim 18 can be removed from instrument 10 and a second spacer block shim that is incrementally smaller than first spacer block shim 18 can be removably attached to instrument 10 and thereafter reinserted in the resection gap G as previously described.

If necessary, the patient's knee joint 200 can be manipulated to adjust the measured gap G and/or the measured angle α between tibia 202 and femur 204. For example, if the surgeon determines that the flexion gap G of FIG. 13 is too small compared to the extension gap G of FIG. 12, the surgeon can cut a deeper posterior femoral resection 210 to increase the flexion gap G of FIG. 13. The surgeon can also make any necessary ligament adjustments to balance the soft tissue around knee joint 200. For example, the surgeon can release the patient's posterior cruciate ligament (PCL), which has been shown to increase the flexion gap G relative to the extension gap G.

FIGS. 12 and 13 depict post-resection use of instrument 10, with instrument 10 being positioned against resected bone surfaces of tibia 202 and femur 204. As discussed above, instrument 10 can also be used pre-resection, with instrument 10 being positioned against natural, un-resected bone surfaces of tibia 202 and femur 204. In this pre-resection condition, instrument 10 can communicate the pre-resection gap G and the pre-resection angle α between the natural, un-resected bone surfaces in extension and flexion. The surgeon can predict the post-resection values by combining the pre-resection values with the planned resections. For example, the surgeon can estimate the post-resection gap G by adding the planned resection depths to the corresponding pre-resection gap G.

The above Detailed Description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more."

In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A knee arthroplasty system for use in a patient's knee joint, the knee joint including a tibia and a femur, the system comprising:
    a spacer block instrument including a base portion, a tibial component extending from the base portion and configured for placement against a tibia, and a femoral component configured for placement against a femur, the femoral component being rotatably coupled to the tibial component; and
    one or more spacer block shims structured for removable attachment to the tibial component.

2. The system of claim 1, wherein each of the one or more spacer block shims comprises a spacer component and a handle portion, wherein the handle portion is structured to be positioned adjacent to the base portion of the spacer block instrument.

3. The system of claim 2, wherein the one or more spacer block shims comprises a plurality of spacer block shims, each of the spacer block shims defining a different shim height.

4. The system of claim 3, wherein the shim height of each of the plurality of spacer block shims is between about 10 mm and about 13 mm.

5. The system of claim 2, wherein each of the one or more spacer block shims includes a connector structured to removably engage, in the alternative, the tibial component of the spacer block instrument.

6. The system of claim 5, wherein the connector is a sliding joint.

7. The system of claim 6, wherein the sliding joint is a dovetail joint.

8. The system of claim 7, wherein the connector includes a ball detent mechanism.

9. The system of claim 2, wherein the base portion of the spacer block instrument includes one or more channels extending through the base portion and configured to receive one or more alignment rods.

10. The system of claim 9, wherein the handle portion of the one or more spacer block shims includes one or more channels configured to at least partially align with the one or more channels in the base portion of the spacer block instrument.

11. The system of claim 2, wherein the handle portion of the one or more spacer block shims includes a fin portion extending in a direction generally perpendicular to an axis of the spacer block instrument.

12. The system of claim 1, wherein the spacer block instrument further comprises a scale plate extending from the base portion and a pointer extending from the femoral component.

13. The system of claim 12, wherein the scale plate includes an arcuate slot configured to at least partially receive the pointer, wherein the pointer travels within the acruate slot as the femoral component rotates relative to the tibial component.

14. The system of claim 13, wherein the scale plate includes a numerical scale defining a range of joint angles.

15. A method of using a knee arthroplasty instrument to evaluate a resected knee joint, the method comprising:
    observing a resection gap between a distally resected femur and a proximally resected tibia;
    selecting a first spacer block shim from a plurality of spacer block shims;
    attaching the first spacer block shim to a tibial component of the knee arthroplasty instrument;
    inserting the knee arthroplasty instrument into the resection gap, including positioning the tibial component and attached first spacer block shim adjacent to the proximally resected tibia and positioning a femoral component of the knee arthroplasty instrument adjacent to the distally resected femur, the femoral component being rotatably connected to the tibial component; and
    evaluating tension in the resected knee joint, including determining a first joint angle formed between the tibial component and the femoral component.

16. The method of claim 15, further comprising:
    removing the knee arthroplasty instrument from the resection gap;
    detaching the first spacer block shim from the tibial component;
    selecting a second spacer block shim from the plurality of spacer block shims;
    attaching the second spacer block shim to the tibial component;
    reinserting the knee arthroplasty instrument into the resection gap; and
    evaluating tension in the resected knee joint, including determining a second joint angle formed between the tibial component and the femoral component, and comparing the first joint angle to the second joint angle.

17. The method of claim 16, wherein each of the plurality of spacer block shims defines a different shim height.

18. The method of claim 15, wherein determining a first joint angle comprises observing a scale plate extending from the knee arthroplasty instrument.

19. The method of claim 18, wherein the scale plate includes an arcuate slot configured to at least partially receive a pointer extending from the femoral component.

20. The system of claim 1, wherein the tibial component is directly rotatably coupled to the femoral component about a post extending from the femoral component along an anterior-posterior axis such that a varus-valgus angle between the tibial component and the femoral component can be measured, wherein a superior-inferior distance between the tibial component and the femoral component is fixed at the post.

* * * * *